United States Patent [19]

Heath, Jr. et al.

[11] Patent Number: 5,235,039

[45] Date of Patent: Aug. 10, 1993

[54] SUBSTRATES FOR HIV PROTEASE

[75] Inventors: William F. Heath, Jr., Indianapolis; Mei-Huei T. Lai, Carmel; Joseph V. Manetta, Indianapolis; John R. Sportsman, Indianapolis; Sau-Chi B. Yan, Indianapolis, all of Ind.

[73] Assignee: Eli Lilly and Company, Indianapolis, Ind.

[21] Appl. No.: 712,828

[22] Filed: Jun. 10, 1991

[51] Int. Cl.$^5$ ............... A61K 37/02; C07K 5/00; C12Q 1/70; C12Q 1/37

[52] U.S. Cl. ............... 530/328; 530/327; 435/5; 435/23; 435/24

[58] Field of Search ............ 435/5, 23, 24; 530/328, 530/327

[56] References Cited

U.S. PATENT DOCUMENTS 4,918,001 4/1990 Kolde .

OTHER PUBLICATIONS

Copeland et al (1990) Biochem Biophys Res Comm 169(1): 310-314.
Geoghegan et al (1990) FEBS 262(1): 119-122.
Wondrak et al (199) Analyt Biochem 188: 82-85.
Stryer (1981) Biochemistry, W. H. Freeman & Co. San Francisco, pp. 14-15.
Kotler et al (1988) PUAS 85: 4185-4189.
Harrison et al (1989) Analyt Biochem 180: 110-113.
Matayoshi et al (1990) Science 247: 954-958.
Wang et al (199) Anti HIV Agents Therapies and Vaccines, vol. 616 of Annals of NY Acad Sci, 617-618.
Twining (1984) Analytical Biochem 143: 30-34.
Bond et al (1986) Analytical Biochem 155: 315-321.
Darke et al (1988) Biochem Biophys Res Comm 156(1): 297-303.
Billich et al (1988) J Biol Chem 263(3): 17905-17908.
Jolley, M. E., et al., *Journal of Immunological Methods*, 67 (1984) 21-35.
MacCrindle, Chris, et al., *Clin. Chem.* 31/9, 1487-1490 (1985).
Bond, M. D., et al., *Analytical Biochemistry* 155, 315-321 (1986).
Kotler, Moshe, et al., *Proc. Natl. Acad. Sci. USA*, vol. 85, pp. 4185-4189, Jun. 1988.
Harrison, R., et al., *Analytical Biochemistry* 180, 110-113 (1989).
Geoghegan, K. F., et al., *FEBS*, vol. 262, No. 1, 119-122, Mar. 1990.
Nashed, N. T., et al., *Biochemical and Biophysical Research Communications*, vol. 163, No. 2, 1989, pp. 1079-1085.
Tomaszek, Jr., T. A., et al., *Biochemical and Biophysical Research Communications*, vol. 168, No. 1, 1990, pp. 274-280.
Sleath, R. A., et al., *Journal of Cellular Biochemistry*, Suppl. 14C, 1990; Abstr., 19th Annual Meetings; Feb. 3-Mar. 11, 1990.

*Primary Examiner*—Christine M. Nucker
*Assistant Examiner*—D. R. Preston
*Attorney, Agent, or Firm*—Paul R. Cantrell; Leroy Whitaker

[57] ABSTRACT

An assay method for the rapid determination of hydrolytic enzyme activity in large numbers of samples is provided which comprises bonding a resin-binding compound, such as biotin, to one side of the scissile bond of the substrate and a reporter molecule, such as a fluorescence marker, to the opposite side of the scissile bond, incubating the modified substrate and the enzyme in multiple well plates, e.g. 96-well plates, optionally in the presence if a test inhibitor or activator compound transferring the incubation solutions to a second multiple well plate having upper and lower chambers separated by a porous membrane the upper chamber of which contains resin beads capable of binding with the resin-binding compound, filtering and washing the wells of the second plate and reading the emission from the plates. The invention also provides protease substrates for HIV-1 protease, vertebrate stromelysin and derivatives thereof which are useful in the assay method.

2 Claims, 2 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
( A ) LENGTH:21 nucleotides
( B ) TYPE:nucleic acid
( C ) STRANDEDNESS:double
( D ) TOPOLOGY:linear ( i i ) MOLECULE TYPE:DNA ( x i ) SEQUENCE DESCRIPTION: SEQ ID NO: 1:

ACTGGAAGGG CTAATTCACT C 2 1

( 2 ) INFORMATION FOR SEQ ID NO: 2:

( i ) SEQUENCE CHARACTERISTICS:
( A ) LENGTH:21 nucleotides
( B ) TYPE:nucleic acid
( C ) STRANDEDNESS:double
( D ) TOPOLOGY:linear (i i) MOLECULE TYPE:DNA (x i) SEQUENCE DESCRIPTION: SEQ ID NO: 2:

ACTGCTAGAG ATTTTCCACA C    21

(2) INFORMATION FOR SEQ ID NO: 3:

(i) SEQUENCE CHARACTERISTICS:
        (A) LENGTH:5 amino acids
        (B) TYPE:amino acid
        (D) TOPOLOGY:linear (i i) MOLECULE TYPE:peptide (i x) FEATURE: The N at position 1 is Ser or Thr, and
                    the N at position 4 is Tyr or Phe.

(x i) SEQUENCE DESCRIPTION: SEQ ID NO: 3:

Xaa Xaa Xaa Xaa Pro
1               5

(2) INFORMATION FOR SEQ ID NO: 4:

(i) SEQUENCE CHARACTERISTICS:
        (A) LENGTH:10 amino acids
        (B) TYPE:amino acid
        (D) TOPOLOGY:linear (i i) MOLECULE TYPE:peptide (x i) SEQUENCE DESCRIPTION: SEQ ID NO: 4:

Gly Ser Gln Asn Tyr Pro Ile Val Gly Lys
1               5                   10

(2) INFORMATION FOR SEQ ID NO: 5:

(i) SEQUENCE CHARACTERISTICS:
        (A) LENGTH:13 amino acids
        (B) TYPE:amino acid
        (D) TOPOLOGY:linear (i i) MOLECULE TYPE:peptide (x i) SEQUENCE DESCRIPTION: SEQ ID NO: 5:

Arg Arg Arg Pro Gln Gln Phe Phe Gly Leu Met Gly Lys
1               5                   10

(2) INFORMATION FOR SEQ ID NO: 6:

(i) SEQUENCE CHARACTERISTICS:
        (A) LENGTH:6 amino acids
        (B) TYPE:amino acid
        (D) TOPOLOGY:linear (i i) MOLECULE TYPE:peptide (x i) SEQUENCE DESCRIPTION: SEQ ID NO: 6:

Arg Arg Arg Pro Gln Gln
1               5

(2) INFORMATION FOR SEQ ID NO:7:

(i) SEQUENCE CHARACTERISTICS:
        (A) LENGTH:7 amino acids
        (B) TYPE:amino acid
        (D) TOPOLOGY:linear (i i) MOLECULE TYPE:peptide (x i) SEQUENCE DESCRIPTION: SEQ ID NO: 7:

Phe Phe Gly Leu Met Gly Lys

SUBSTRATES FOR HIV PROTEASE

BACKGROUND OF THE INVENTION

This invention relates to an assay method for determining hydrolytic enzyme activity and to polypeptides and modified polypeptides useful therein. In particular, it relates to a method for determining hydrolytic enzyme activity which is applicable to the rapid screening of large numbers of potential enzyme inhibitors or stimulators.

The availability of methods for the evaluation of hydrolytic enzymes not only permits the study of the enzyme itself, for example its activity against modified substrates or its kinetics, but also provides for evaluating substances as inhibitors or stimulators for enzymes. Methods for the rapid screening of hydrolytic enzyme inhibitors and stimulators exist where the recognition sites for the enzyme are on one side of the cleavage site of the substrate. For example, in a tetrapeptide

A—B—C—D—X, wherein X is a marking element e.g. a fluorescent marker, and A, B, C, and D represent amino acid residues, any protease that cleaves at the C-terminal side of residue D with recognition sites in the residues N-terminal to D will release the marker X which, when released, will exhibit a different absorption spectrum and can be readily detected in the visible spectrum. The intensity of the absorption will correspond to the extent cleavage has occurred. Accordingly one can screen for inhibitors of such a protease by simply adding the inhibitor to the protease reaction mixture and directly measuring the extent of cleavage. Numerous potential inhibitors thus can be screened rapidly. When, however, the protease requires recognition sites on both sides of the cleavage site such as shown below

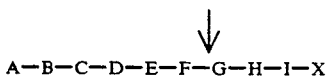

A—B—C—D—E—F—G—H—I—X wherein A-I are amino acid residues and X is the marker, then X will not be released, as described above, to provide the requisite absorption change to measure the extent of cleavage. Thus, the extent to which cleavage occurred has to be determined indirectly, e.g. by chromatographic analysis such as with HPLC. Accordingly, prior to the present invention there was no adequate method available for rapidly screening hydrolytic enzyme inhibitors or stimulators where the enzyme requires recognition elements on both sides of the cleavage site of the substrate.

The method of this invention is applicable to hydrolytic enzymes in general and can be used, for example, in assaying for proteases, glycosidases and nucleases.

DETAILED DESCRIPTION

Figure 1:
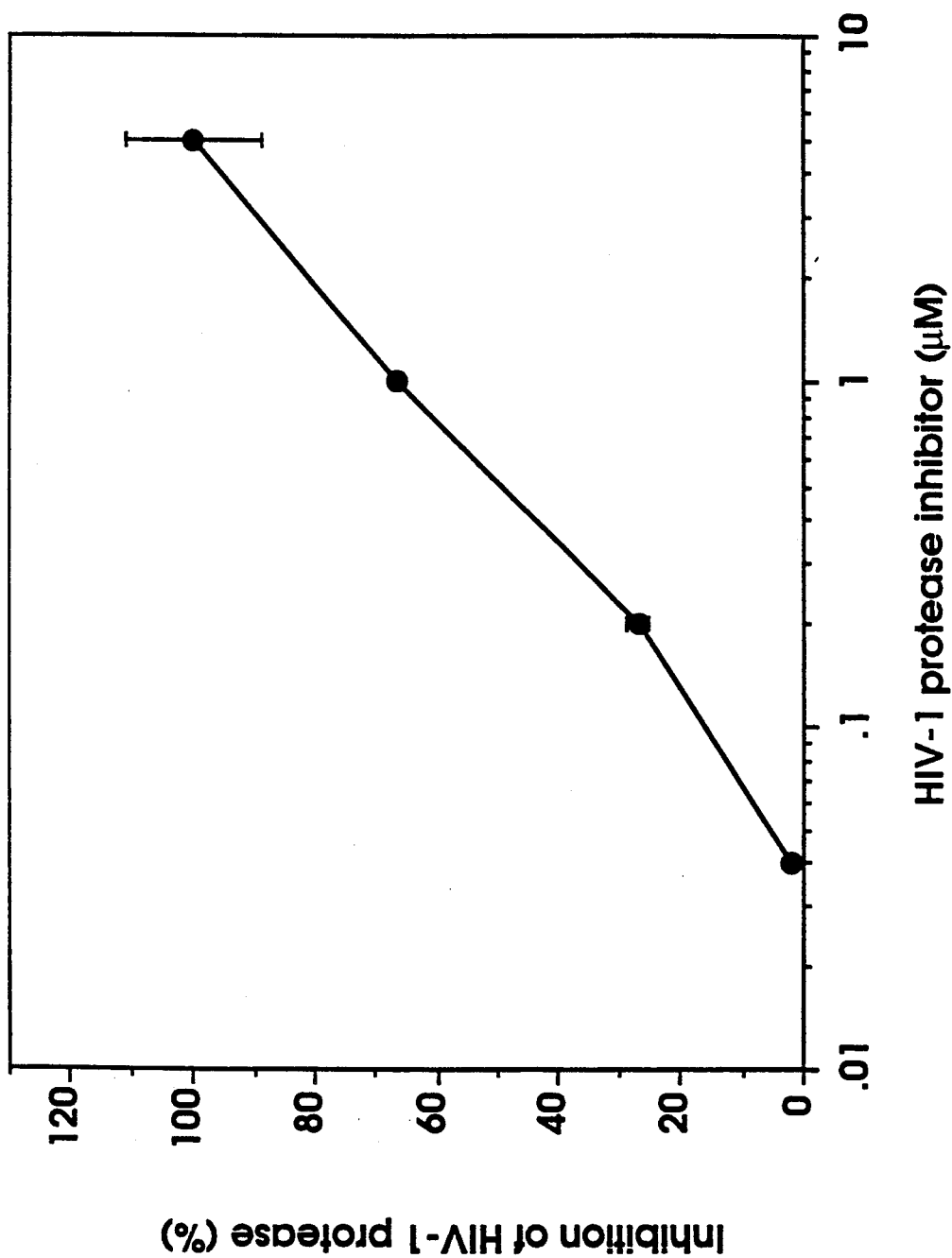
FIG. 1 of the drawings is a plot of the percent inhibition of HIV-1 protease vs the concentration of a known HIV-1 protease inhibitor obtained in the assay method described herein.

According to the method of this invention, the enzymatic activity of hydrolytic enzymes against substrates specific for the enzyme is measured rapidly and accurately in a variety of assay samples. The method comprises the use of modified substrates wherein a resin-binding compound is bonded to the substrate on one side of the cleavage site and a reporter compound is bonded on the other side of the cleavage site. The modified substrate is incubated with the hydrolytic enzyme until hydrolysis is complete. The hydrolysis mixtures thus comprise a hydrolysis fragment bonded to the resin-binding compound and a fragment bonded to a reporter compound.

The hydrolysis mixture is transferred to the well of an assay plate wherein the well comprises an upper chamber and a lower chamber separated by a permeable membrane. The upper chamber of the well contains resin beads capable of binding with high affinity, and preferable irreversibly, with the resin-binding compound. The resin beads are of such size as to preclude their passage through the membrane separating the chambers. The hydrolysis mixture is added to the upper chamber containing the resin beads and the well is washed and the wash is filtered through the membrane. The hydrolysis fragment of the substrate bonded to the resin-binding compound is secured in the upper chamber by binding to the resin beads present. The fragment of the substrate bonded to the reporter compound is washed and filtered through the membrane into the lower chamber. The extent to which hydrolysis of the substrate occurred is then measured by determining the level of emission of the reporter compound present in the upper chamber.

The assay method of this invention is especially useful in the rapid determination of hydrolytic enzyme activity in multiple samples. The method is particularly useful in the determination of the activity of inhibitors and stimulators of hydrolytic enzymes. The method is applicable in such contexts for determining the activity of hydrolytic proteases on homopolymers of different amino acids (peptides), the activity of nucleases on homopolymers of different nucleic acids and, the activity of glycosidases on homopolymers of different sugar residues or on heteropolymers of sugar residues and amino acid residues. The applicability of the method to hydrolytic enzymes of other substrates will be readily appreciated from the description of the method provided herein.

The following llustrates the foregoing description of the assay method provided herein.

{X or Y} A—B—C—D—E—F—G—H—I {X or Y}

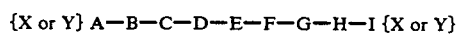

In the above formula representing the enzyme substrate the arrow indicates the cleavage site; A to I represents a homopolymer of different amino acids or, a homopolymer of different nucleic acids of the bases adenine, cytosine, guanine and thymidine or, a homopolymer of different sugar residues or, a heteropolymer of sugar residues and amino acid residues; X represents the reporter compound and Y represents the resin binding compound. The parenthetical X or Y on both sides of the cleavage site indicates that one of X or Y can be bonded to the substrate A–I on either side of the cleavage site. For example, when A–I is a polypeptide the resin binding compound can be bonded to the peptide on either side of the cleavage site while the reporter compound X is bonded on the opposite side and vice versa. The point of attachment of X or Y on either side of the cleavage site may vary depending upon the particular substrate. For example, the resin binding compound can be attached at the amino group of the amino terminus end of a peptide or, alternatively, at the amino group of an amino acid elsewhere on the amino terminus side of the scissile bond.

Assuming attachment of the reporter compound X to the right of the cleavage site (e.g. the carboxy terminus of a peptide), after cleavage of the modified substrate by the protease, nuclease or glycosidase, the hydrolysis products are represented by the following general formulae.

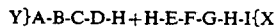

Y}A-B-C-D-H+H-E-F-G-H-I{X

When complete hydrolysis of the modified substrate has occurred the cleavage product Y}A-B-C-D-H is bound to the resin in the upper chamber of the assay well while the cleavage fragment H-E-F-G-H-I}X is washed through and removed from the well. Accordingly there will be no emission attributable to the reporter compound upon measurement demonstrating complete hydrolysis by the enzyme. The extent to which hydrolysis is incomplete during incubation is determined by measuring level of emission arising from resin bound unhydrolyzed substrate in the upper chamber after washing and filtration.

The method of this invention can be used to screen large numbers of potential enzyme inhibitors for example protease inhibitors. The method also has wide applicability in the screening of potential enzyme stimulators or activators. For example, the effect of activator substances or test substances as activators in releasing competent enzyme from a zymogen or proenzyme can be rapidly measured. The method can be used to screen fermentation broths and cell-conditioned media for the presence of enzymes, e.g. proteases, or to detect protease activity in various other biological fluids.

The method described herein utilizes the commercially available Pandex automated Reader instrument for immunoassays. The Pandex instrument is equipped with 96-well plates with each well having an upper chamber separated from a lower chamber by a membrane having a size exclusion of about 0.2 microns to about 0.5 microns. The instrument can pipette reagents into the 96 wells, wash, evacuate the plates, and can read fluorescence emissions from the plates.

In practicing the method the enzyme substrate having enzyme recognition sites on both sides of the cleavage site is bonded on one side of the cleavage site with a reporting molecule (marker) and on the other side with a resin-binding compound. The marked substrate is dissolved in a buffer to a desired concentration and the solution is added via pipette to each well of a multiple well incubation plate containing the enzyme and a test compound. As noted above the test compound may be a potential inhibitor of the enzyme or a potential activator. In the latter instance the substrate is mixed in the wells with the zymogens and the potential activator as the test compound. After incubation for a period of time appropriate for the particular enzyme-substrate reaction the incubation mixture is diluted with buffer and transferred into each well of a 96-well Pandex plate each well of which contains resin for immobilization in the upper chamber. The plates are then loaded into the Pandex instrument and are washed and read.

The foregoing generalized description of the method can be illustrated by the scheme below.

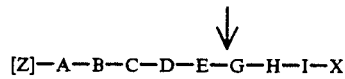

[Z]—A—B—C—D—E—G—H—I—X wherein Z represents the immobilizing resin attached to A via the resin-binding compound, A-E and G-I represent amino acid residues, X is a fluorescence marker or other reporting compound and the arrow shows the cleavage site. Upon cleavage and after washing the 96-well Pandex plates the resin-bound amino terminus end [Z]-A-B-C-D-E is held by the porous membrane in the upper chamber of each well while the marked carboxy terminus end, G-H-I-X, is washed into the lower chamber. Thus the extent of cleavage is measured, via standard curves, by the level of fluorescence remaining in the wells after washing and evacuation.

The substrate marker or reporting compound can be any conventional marker preferably a fluorescence marker such as is obtained by reacting the substrate with fluorescein isothiocyanate (FITC) or fluorescamine. It will be appreciated that other marking means may be employed such as for example use of a radioactive labeled ester or a UV absorbing compound. The fluorescent FITC is a preferred marker owing to its strong emission which allows for greater sensitivity in measuring the extent of substrate cleavage at very low concentrations.

The immobilization of the modified substrate, and thus its retention in the upper chamber of the Pandex plate wells, must be via high affinity binding or preferably, irreversible binding, under the conditions of the assay. Although other methods of immobilizing the substrate will be appreciated the preferred immobilization of this invention employes polystyrene beads coated with the glycoprotein avidin. The resin-binding compound bonded to the substrate is preferably biotin. The biotin attached to the substrate binds tightly and rapidly to the avidin coating on the resin beads to form an irreversible binding of the substrate or the portion thereof resulting from cleavage. The resin beads are of a diameter such as to restrict their passage through the membrane separating the upper and lower chambers of the Pandex plate wells. The diameter of the resin beads is between about 0.6 to about 1.0 micron and preferably between about 0.6 to about 0.8 microns.

The assay method provided by this invention has wide applicability to the study of hydrolytic enzymes. In one embodiment of the invention the activity of glycosidases is measured. In this embodiment in the foregoing formula, A-I represents a homopolymer of different sugar residues. The polymer substrate (oligosaccharide) may be linear or branched. These polymers possess a reducing end (right end of formula A-I above) and the sugar at the left end is referred to as the non-reducing end. The sugars at the reducing end contain free aldehyde groups which are absent in the sugars at the non-reducing end. In a specific example of the assay for glycosidases, the glycosidase β-D-mannoside mannohydrolase (E.C.3.2.1.25) hydrolyses the branched oligosaccharide represented by the following formula with the indicated specificity.

```
Gal—GlcNac—Man
              \
               >Man B₁ —>₄GlcNac B₁ —>₄GlcNac
              /           ↑
Gal—GlcNac—Man

---Man B₁ —>₄Man

---Man B₁ —>₄GlcNac

---Man B₁ —>₄Glc---Cer

---Man B₁ —>₄GlcNac B₁ —>₄GlcNac₆ <—₁a Fuc
``` wherein
Gal = galactose
Man = mannose
GlcNac = N-acetylglucosamine
Glc = glucose
Fuc = fucose
Cer = ceramide The β-D-mannoside mannohydrolase is obtained from snails (Achatina fulica) and is described by Yamashita, K., et al., (1982) *Meth. Enzymol.* 83 105. Other glycosidases which can be assayed by the method provided herein and their specificity are described by Montreuit et al., (1986) in Carbohydrate Analysis—a practical approach. Ed. by Chaplin, M. F. and Kennedy, J. F., IRL Press and Hopwood, J. J. (1989) Chapter 10 in Heparin:chemical and biological properties, clinical applications. Ed. by Lane, D. A., and Lindahl, V., CRC Press.

As described hereinabove the method provided can be used to measure the activity of hydrolytic enzymes of heteropolymers represented in general by the foregoing formula A-I. For example, the heteropolymer can be represented by the formula

```
B₂—B₁—B          ↓
         \
          C—D—E—F—H—I
         /          |
A₂—A₂—A             G
``` wherein A-E are sugar residues, F-I are amino acid residues and the arrow indicates the cleavage site. A particular example of this application of the method comprises measuring the activity of the enzyme peptide: N-glycosidase F(E.C.3.2.2.18) which is obtained from *Flavobacterium meningosepticum*. With reference to the above general formula for the sugar:amino acid heteropolymer this enzyme's specificity is such that:
D = GlcNac β₁→₄
E = GlcNac β₁→
F = Asn (wherein the side chain carboxamide group is linked to E)
G, H and I = any amino acid residues
A₂ and B₂ = galactose
A₁ and B₁ = GlcNac
A, B and C = mannose Other examples of glycosidases the activity of which can be measured rapidly and accurately in the method of this invention are described by Tarentino et al. (1989) *Methods in Cell Bioloy* 32 111-139.

The method of this invention also can be used to measure the activity of nucleotide hydrolytic enzymes. An example of a nucleotide hydrolytic enzyme that requires specific recognition sequences is HIV-1 integrase. Integrase is essential for the integration of the HIV-1 genome into the host chromosomes. The enzyme is an endonuclease which recognizes short stretches of sequences located at the 5' and 3' end of the long terminal repeats (LTR) of the viral DNA. The specific sequences are illustrated below:

| Substrate | Oligonucleotide Sequence |
|---|---|
| LTR 5' | 5'ACTGGAAGGGCTAATTCACTC 3'<br>3'TGACCTTCCCGATTAAGTGAG 5'<br>↑<br>(Seq. I.D. NO. 1) |
| LTR 3' | 5'ACTGCTAGAGATTTTCCACAC 3'<br>3'TGACGATCTCTAAAAGGTGTG 5'<br>↑<br>(Seq. I.D. NO. 2) | wherein the arrows indicate the cleavage sites and A, T, G and C denote adenine, thymine, guanine and cytosine respectively.

The preparation of modified substrates for use in the assay method of this invention is carried out by conventional preparative methods. A peptide substrate for protease can be reacted with a reporter molecule at a functional group of the peptide on either side of the scissile bond and the resin-binding compound bonded to a functional group of the peptide on the opposite side of the scissile bond. For example, the reporter compound and the resin-binding compound can be reacted with the peptide substrate to form stable linkages with the N-terminal amino group, the C-terminal carboxylic acid or with a functional group of an amino acid residue within the peptide sequence such as a thiol group of cysteine, the carboxylic acid groups of an aspartic acid residue, or a glutamic acid residue, an amino group of lysine, the guanidino group of arginine, the imidazole group of histidine, the indole group of tryptophan, and the phenolic group of tyrosine. The particular choice of the bonding site and the reaction conditions employed will depend upon the particular substrate, the resin-binding compound and the reporter molecule. For example, the resin-binding compound biotin, can be condensed with any of the amino groups of the amino acid residues described above. The carboxylic acid group of biotin readily forms an amide bond with such amino groups. Biotin can also be reacted with the hydroxy group of a tyrosine residue or a thiol group of cysteine to form an ester linkage. Likewise fluorescein as the isothiocyanate derivative can be reacted with an amino group of an amino acid residue of the peptide substrate to form stable derivatives. Fluorescein as a carboxylic acid derivative can likewise form stable amides with such amino groups and stable esters with the hydroxy group and thiol groups. An amino substituted fluorescein reporter compound can be condensed with free carboxylic acid groups of amino acid residues to form stable amide bonds.

Heteropolymers of peptides and sugar residues such as described hereinabove can be derivatived with resin-binding compounds and reporter compounds in the peptide portion of the substrate as described hereinabove. The sugar moieties of the heteropolymer can be derivatized at reactive aldehyde groups or hydroxy groups of the sugar residues. For example, an aldehyde group can be reduced e.g., with a borohydride, to form an intermediate hydroxymethyl substituted sugar residue and the latter reacted with the carboxylic acid group of a resin-binding compound e.g. biotin. Alternatively, the aldehyde group of a sugar residue can be reacted with an alkyl diamine such as propylenediamine to form an imine with one of the amino groups. The imine is reduced to form the saturated 3-aminopropylaminomethyl derivative of the sugar residue. The free amino group of the derivative thus provided is then available for reaction with a reporter compound or a resin-binding compound. Thus conventional preparative methods can be used to prepare modified heteropolymeric substrates wherein the scissile bond is between the peptide portion and the sugar polymer portion.

Homopolymers such as oligosaccharide substrates can be modified likewise for use in the assay by conventional methods. For example, when the polymer A-l is an oligosaccharide the free reducing aldehyde end group is reacted with an alkyl diamine $NH_2(CH_2)_nNH_2$ and the intermediate imine is reduced e.g., with sodium cyanoborohydride, to provide an aminoalkylaminomethyl derivative as shown below.

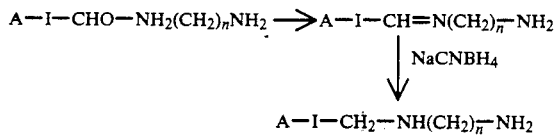

wherein n is a divalent alkylene linkage e.g. of from 1-10. The reductive amination method for preparation of the aminoalkyl linker group is described by Wang, W. T. et al. (1984) *Anal. Biochem.* 141 366-381. The free amino group of the linker then can be reacted with a reporter compound or a resin-binding compound.

The oligosaccharide substrate also can be derivatized e.g., with the resin-binding compound biotin, at the non-reducing end (residue A) of the polymer A-l as follows. Frequently the non-reducing end (residue A) of an oligosaccharide is galactose. If not present galactose can be placed on the reducing end during the preparation of the polymer or attached to the existing (natural) polymer. The hydroxyl group on the 6-carbon of the galactose residue can be quantitatively oxidized to the aldehyde group with the commercially available galactose oxidase (Sigma Chemical Co.). Thereafter by employing the reductive amination procedure described above the aminoalkyl linker is provided on the non-reducing end of the oligosaccharide for reaction with either a reporter compound or a resin-binding compound as described hereinabove.

The oligonucleotide substrates for endonuclease are modified for use in the assay by reacting the reporter compound and the resin-binding compound with the amino groups of the nucleic acid bases or with free terminal phosphoric acid groups.

The method of this invention is particularly useful for screening various substances as enzyme inhibitors. For example, the method is used to particular advantage in rapidly screening large numbers of compounds for activity as protease inhibitors.

In carrying out the assay method of this invention to measure the inhibitory activity of substances against protease, the substrate peptide, substituted with the resin-binding compound and the marking compound, is incubated with the protease in the presence of the test compound. Multiple-well plates for example, 96-well plates, are utilized in the method to carry out the proteolytic cleavage of a given substrate in the presence of numerous test compounds being screened for inhibitory activity. Also the activity of test substances can be readily determined at various concentrations. Owing to the versatility of the method it is possible to assay for inhibitory activity vs different substrates and proteases on the same multiple-well plate.

After the incubation period for the protease-substrate reaction the incubation mixtures containing the cleavage products in the multiple wells are transferred to the wells of the 96-well Pandex plate. The incubation mixtures may require dilution prior to transfer to the Pandex wells. Transfer of the mixtures and dilution are readily accomplished by microtitration. Each of the 96-wells in the Pandex plate contain a suspension of prepared resin beads for binding with the resin-binding compound attached to the peptide substrate. The preferred resins are polystyrene beads coated with avidin. These coated beads form an irreversible binding with the preferred resin-binding compound biotin. It will be appreciated however that other resins and binding compounds can be employed. For example, it is possible to construct the membrane separating the upper and lower chambers of the Pandex plates with the resin to which the resin-binding compound attaches.

After the incubation mixtures are added to the Pandex wells the mixture is mixed in the wells with the resin beads to effect binding with the resin-binding compound. The plates are then loaded into the Pandex instrument, washed with a suitable buffer and read.

A specific embodiment of the invention comprises carrying out the assay method to discover and study inhibitors of HIV-1 protease. Recent studies show that inhibition of the HIV-1 protease blocks production of infectious virus. The natural substrate of this protease is the gag-pol precursor protein which is cleaved into four core proteins and the essential enzymes HIV-1 protease, reverse transcriptase, ribonuclease H, and endonuclease. One consensus sequence for this cleavage is (Ser/Thr)-Xaa-Xaa-(Tyr/Phe)-Pro, (Seq. I.D. No. 3) in which cleavage occurs N terminal to Pro. In this embodiment of the invention a decapeptide analog of the natural scissle region is employed to screen for inhibitors of the HIV-1 protease. The decapeptide is represented by the formula Gly-Ser-Gln-Asn-Tyr-Pro-Ile-Val-Gly-Lys-OH (Seq. I.D. No. 4) and is cleaved by the protease between the Tyr-Pro portion.

For use in the assay the N-terminus of the decapeptide is coupled with biotin and the ε-amino group of the C-terminal lysine is reacted with the fluorescent marker, fluorescein isothiocyanate to provide the modified peptide represented by the formula $N^\alpha$-Biotin-Gly-Ser-Gln-Asn-Tyr-Pro-Ile-Val-Gly-Lys-$N^\epsilon$-(FITC)-OH (Seq. I.D. No. 4).

The modified decapeptide is dissolved in a suitable buffer at a pH between about 5 and about 6 to form a solution at a desirable concentration, e.g. about 1.5 μg/ml. A separate solution of the protease in the same buffer is prepared at a sufficient concentration of protease to hydrolyze all substrate. To each well of a round-bottom, 96-well plate, e.g. a polystyrene microtiter plate, is added the enzyme solution followed by a buffered solution of the inhibitor compound. The solution of the inhibitor may be diluted in 20% aqueous dimethylsulfoxide when necessary for solubility. The plates are allowed to stand for about one hour at about room temperature before the substrate solution is added to each well. The plates are allowed to stand for about 8 h to about 16 h at about room temperature during which time the protease hydrolyzes the substrate unless inhibited by the test compound. Thereafter the reaction mixture in each well is diluted with buffer and a portion of the diluted reaction mixture is added to each well of the Pandex 96-well plate each well of which contains a solution of the avidin coated resin beads in buffer. The contents of the wells are mixed to complete binding to the resin. The plates are loaded into the Pandex Model 784 Screen Machine (supplied by Baxter Healthcare). Unbound fluorescence is removed by filtration and subsequent washing with buffer. Any bound fluorescence is detected by excitation at 485 nm and reading the resulting epifluorescence at 535 nm. The amount of fluorescence indicates the extent to which the enzymatic reaction is inhibited.

As described hereinabove the Pandex Plates used in the assay method are 96-well two-chamber plates (upper and lower chambers) wherein the chambers are separated by a 0.2 $\mu$M pore size membrane. Suction applied to the plate draws the fluid from each well through the membrane and into the bottom chamber. The resin bound substrate or cleaved portion thereof is retained by the membrane. The wells are then automatically washed twice and are dried. Any fluorescent marked cleavage fragment (unbound fluorescence) in the wells is washed from the well and out of the plate.

The method of this invention may be referred to as a particle concentration fluorescence assay method. Particle concentration fluorescence involves the binding and concentration of a fluorescent moiety to a solid particle followed by the isolation of the particles from the reaction solution and quantitation of the signal using epifluorescence. Since the fluorescent entity is isolated from the solution, common problems of fluorescent measurement because of contaminating interference is minimized.

FIG. 1 of the drawings is a plot of the results obtained in the HIV-1 assay method of this invention with the known HIV-1 protease inhibitor, Ac-Nal-Pro-Phe-Val-Sta-Leu-Phe-NH$_2$, wherein Ac=acetyl, Nal=naphthylalanine, and Sta=statine. The plot shows the percent inhibition of the protease vs the concentration ($\mu$M) of the inhibitor. As is shown 100% inhibition was obtained with the inhibitor at a concentration of about 7 $\mu$M.

A further aspect of the invention comprises the use of the assay method for measuring the amount of hydrolytic enzyme activity in samples. In this use of the method the generation of protease or, in general, enzyme activity from an enzyme source can be readily determined in a large number of samples. For example, the effect of activator substances or test substances as activators or as inhibitors of activators in releasing competent enzyme from a proenzyme or zymogen can be readily and quickly measured. According to this aspect of the invention, the source of the enzyme may be incubated in the presence of an activator substance and the modified substrate specific for the generated enzyme.

Alternatively, the enzyme source may be treated separately to produce the enzyme which is then incubated in the presence of the modified substrate. Numerous proenzymes and activators thereof are know. The assay method provided herein allows one to screen for potential activators, as well as inhibitors of known activators of proenzymes.

In specific embodiments of this use of the method the level of procollagenase and prostromelysin secreted by fibroblasts in response to stimulation is readily measured. Stimulation of the enzyme protein kinase C with 4$\beta$-phorbol, 12,13-dibutyrate (PDBu) causes human fibroblasts to produce and secrete the enzyme precursors, procollagenase and prostromelysin. The stimulation of protein kinase C and the subsequent production and release of these precursors occurs in a PDBu dose-dependent manner. While these precursors lack enzymatic activity, incubation of the precursors with an organomercurial compound e.g. 4-aminophenylmercuric acetate leads to the formation of the enzymatically competent proteins, vertebrate collagenase and vertebrate stromelysin.

In the vertebrate collagenase assay of this invention use is made of the substrate, Pro-Gln-Gly-Ile-Ala-Gly-D-Arg-Lys-OH. This substrate is cleaved by vertebrate collagenase at the Gly-Ile bond to form the Pro-Gln-Gly-OH tripeptide and the H-Ile-Ala-Gly-D-Arg-Lys-OH pentapeptide. According to the practice of this invention the vertebrate collagenase substrate is bonded to biotin, preferably at the amino terminus, and is labelled with the fluorescence marker on the $\epsilon$-amino group of lysine by reaction with fluorescein isothiocyanate to form the modified substrate, N$^\alpha$-Biotin-Pro-Gln-Gly-Ile-Ala-Gly-D-Arg-Lys-(N$^\epsilon$-FITC)-OH.

A buffered solution of the modified substrate containing 4-aminophenylmercuric acetate is mixed with a buffered conditioned medium containing the fibroblast produced procollagenase in each well of a 96-well incubation plate and the mixture is incubated for about 16 hours at about 37° C. After incubation a portion of the solutions are transferred to each well of a fresh 96-well plate, are diluted with buffer, and further incubated for about 30 minutes at about room temperature. The diluted reaction solutions are added to the 96-wells of a Pandex plate each containing a solution of avidin coated polystyrene beads and the solutions are mixed well. The plates are loaded into the Pandex machine and are washed with buffer and read for fluorescence.

The vertebrate collagenase assay provides a rapid and accurate measurement of the amount of cell generated procollagenase.

The assay method of this invention for measuring prostromelysin formation is carried out as described above for the procollagenase assay method.

The stromelysin substrate, Arg-Arg-Arg-Pro-Gln-Gln-Phe-Phe-Gly-Leu-Met-Gly-Lys-OH (Seq. I.D. No. 5), is hydrolyzed by stromelysin at the Gln-Phe position to form the hexapeptide, Arg-Arg-Arg-Pro-Gln-Gln-OH (Seq. I.D. No. 6) and the heptapeptide, H-Phe-Phe-Gly-Leu-Met-Gly-Lys-OH (Seq. I.D. No. 7). The modified substrate, Biotin-Arg-Arg-Arg-Pro-Gln-Gln-Phe-Phe-Gly-Leu-Met-Gly-Lys-($\epsilon$FITC)-OH (Seq. I.D. No. 4), is prepared for use in the assay.

Figure 2:
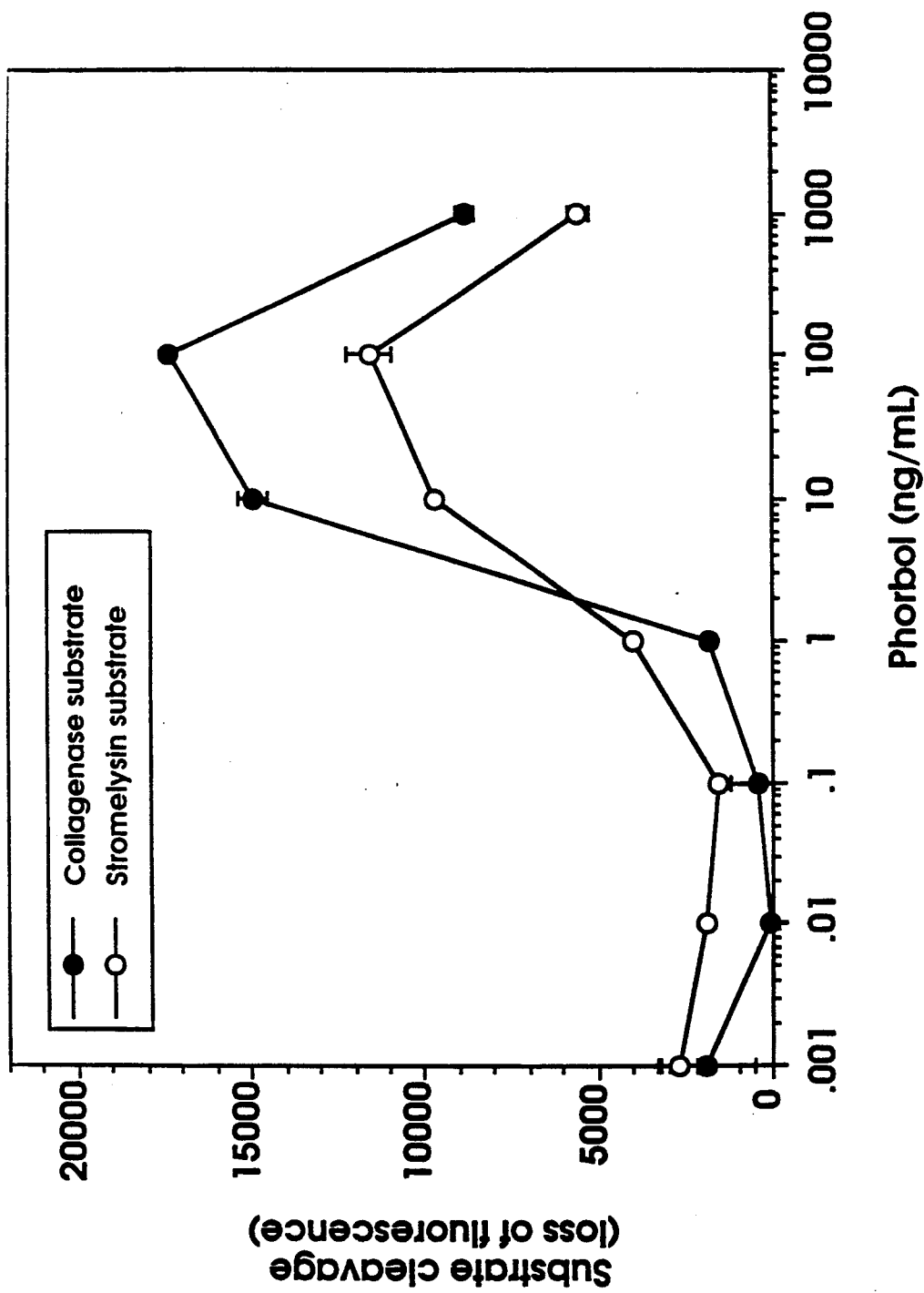
FIG. 2 of the drawings is a plot of the loss of fluorescence observed in the assay method for measuring the amount of procollagenase and prostromelysin formed in response to the concentration of phorbol induced secretion of the proenzymes.

FIG. 2 of the drawings is a plot of the results obtained in the assay for vetebrate collagenase and stromelysin. The figure shows the effect of the phorbol ester concentration on the secretion of procollagenase and stromelysin by human fibroblasts and is measured by the loss in fluorescence caused by substrate hydrolysis by the collagenase and stromelysin generated in the assay. As shown, when the phorbol concentration reaches about 1 to 10 ng/ml secretion of the proenzyme from fibroblasts rises rapidly.

One aspect of this invention provides a method for rapidly measuring the amount of a hydrolytic enzyme generated or released by a proenzyme in multiple samples wherein the substrate for said enzyme comprises recognition sites on both sides of the cleavage site which comprises;

a) incubating in multiple reaction chambers a proenzyme with an activator in the presence of said substrate and wherein the substrate is bonded on one side of the cleavage site with a resin-binding compound and on the opposite side with a reporter compound;

b) transferring the incubation solutions from each reaction chamber to a multiple-well plate wherein the wells have an upper and lower chamber separated by a porous membrane, wherein each upper chamber of said wells contains a solution or suspension of resin beads capable of irreversible binding to said resin-binding compound bonded to the substrate and, wherein the size of said resin beads precludes passage of the bound substrate or hydrolyzed resin bound portion thereof through said membrane;

c) filtering and washing each of said two-chambered wells; and d) measuring emission in each well of said plate.

As described herein, when the method is used to determine inhibiting activity of test compounds step a) of the process is carried out in the presence of the test compound. When the method is employed to assay for the generation of a hydrolytic enzyme from a zymogen with an activator the incubation is carried out in the presence of a zymogen and the activator. The assay method provided by this aspect of the invention has general applicability and can be best used for the rapid screening of many test activator compounds. The method is also highly sensitive and reproducible. The assay may be used in screening for inhibitors of a wide variety of proteases such as the rhinovirus protease, renin protease, thrombin, elastase, chrymotrypsin aned kallikrein.

The assay method of this invention for determining inhibitory activity of test compounds thus comprises the steps:

a) incubating in a multiple-well plate in the presence of a test compound a protease and a substrate for said protease wherein said substrate is bonded on one side of the cleavage site with a resin-binding compound and on the opposite side with a reporter molecule;

b) transferring the incubation solutions from each well of the multiple-well plate to a second multiple well plate wherein the wells have an upper and lower chamber separated by a porous membrane, wherein each upper chamber of said wells contains a solution or suspension of resin beads capable of irreversible binding to said resin-binding compound bonded to the substrate and wherein the size of said resin beads precludes passage of the bound substrate, or the hydrolyzed portion thereof bonded to the resin, through said membrane;

c) filtering and washing each of said two-chambered wells; and d) measuring the emission in each well of said second plate.

It will be recognized by those in the art that the conditions of incubation i.e. time, temperature and pH will vary somewhat depending upon the particular protease-substrate reaction. Typically, standard buffers are employed in the incubations which are in general carried out at mild temperatures of about room temperature to about 40° C.

In transferring the incubation solutions to the wells in the second multiple well plate the incubation mixture can be diluted with a suitable buffer to provide a desirable concentration.

The preferred resin-binding compound of the invention is biotin. A preferred reporter compound is a fluorescence marking compound such as that formed with the substrate and fluorescein isothiocyanate. Preferred resin beads are polystyrene beads coated with avidin which are commercially available (Fluoricon Avidin Assay Particles; Baxter Healthcare).

The method of this invention is best carried out with the use of a Pandex Model 784 Screen Machine (Baxter Healthcare).

The resin beads employed in the process when Pandex multiple well plates are used have a diameter between about 0.5 to about 0.8 microns.

A preferred embodiment of the assay method of this invention is that described hereinabove for measuring the inhibitory activity of compounds against HIV-1 protease. Other embodiments of the invention are the vertebrate collagenase and stromelysin assay methods.

The invention in a further aspect provides novel protease substrates and modified substrates for use in the method of the invention which are represented by the following formulae,

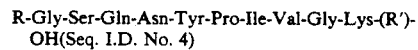

R-Gly-Ser-Gln-Asn-Tyr-Pro-Ile-Val-Gly-Lys-(R')-OH(Seq. I.D. No. 4)

R-Pro-Gln-Gly-Ile-Ala-Gly-D-Arg-Lys-(R')-OH

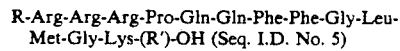

R-Arg-Arg-Arg-Pro-Gln-Gln-Phe-Phe-Gly-Leu-Met-Gly-Lys-(R')-OH (Seq. I.D. No. 5)

wherein R is hydrogen or the biotinoyl group and R' is hydrogen or FITC.

As described therein these substrates and the modified forms thereof are useful in the assay method of this invention to screen for protease inhibitors.

The following Preparations and Examples are provided to further illustrate the invention and are not intended to be limitation thereof.

The following abbreviations used in the Preparations and Examples have the following meanings.

BSA-bovine serum albumin
BOC-t-butyloxycarbonyl
BrZ-2-bromobenzyloxycarbonyl
2-ClZ-2-chlorobenzyloxycarbonyl
DCC-dicyclohexylcarbodiimide
DIEA-diisopropylethylamine
DMSO-dimethylsulfoxide
DTT-dithiothreitol
EDTA-ethylenediaminetetraacetic acid
FITC-fluorescein isothiocarbamyl
FAB-MS-fast atom bombardment mass spectrum
HEPES-4-(2-hydroxyethyl)-1-piperazineethanesulfonic acid
MES-4-morpholineethanesulfonic acid
PAM-phenylacetimidomethyl
TAPS-3-[tris(hydroxymethyl)methyl]amino-1-sulfonic acid
TRIS-tris(hydroxymethyl)aminomethane
TOS-p-toluenesulfonyl (tosyl)

Preparation of Protease Substrates

Preparation 1

N$\alpha$-Biotin-Pro-Gln-Gly-Ile-Ala-Gly-D-Arg-Lys(N$\epsilon$-FITC)-OH

Substrate for Vertebrate Collogenase

The protected peptide-resin, N$\alpha$-Boc-Pro-Gln-Gly-Ile-Ala-Gly-D-Arg(Tos)-Lys(2-CIZ)-OCH$_2$-PAM resin, was prepared on an Advanced Chemtech Model 200 peptide synthesizer at 1.5 millimole scale using the standard double-couple protocol. The amino terminal Boc group was removed with 50% trifluoroacetic acid in methylene chloride and the resulting resin was neutralized with 5% diisopropylethylamine in methylene chloride. Then 1.1 g of biotin (4.5 mmol) was dissolved in 20 of DMSO and the solution added to the peptide resin. Next, a solution of 4.5 ml mmole of DCC in 9 ml of methylene chloride was added to the resin and the mixture was diluted with 11 ml of methylene chloride to a total volume of 40 ml. The coupling reaction was allowed to proceed for 5 h. The reaction solution was removed, the resin washed with DMSO, DMF and methylene chloride, the resin neutralized with 5% DIEA in methylene chloride, and the reaction repeated twice more with the reaction time being extended to 12 h for each reaction. The final peptide resin was washed extensively with DMF and methylene chloride and dried. There were obtained 3.63 g (92% yield) of the protected biotin coupled-peptide-resin.

The peptide was deprotected and cleaved from the resin using 50 ml of HF/m-cresol, 9:1, at 0° C. for 1 hr. After removal of the HF by vacuum distillation, the m-cresol was extracted with 100 ml of diethyl ether. The peptide was solubilized in 50% aqueous acetic acid, frozen and lyophilized. There were obtained 1.79 g of the peptide, N$\alpha$-Biotin-Pro-Gln-Gly-Ile-Ala-Gly-D-Arg-Lys-OH.

The crude freeze dried peptide was dissolved in 200 ml of 0.1% trifluoroacetic acid in water:acetonitrile, 90:10 v/v, the solution filtered through a 0.22 micron filter and applied to a 2.2×25 cm reverse phase column of octadecyl-silica (Vydac C-18) previously equilibrated with the same buffer. The peptide was eluted with a 855 minute linear gradient of 5 to 20% acetonitrile at 2 ml/min. with collection of fractions. Analytical high-performance liquid chromatography was performed on a 4.6×250 mm Vydac C-18 column using similar buffer conditions to analyze the column fractions. Fractions containing the desired material were pooled, frozen and lyophilized. Final yield of purified peptide was 1.27 g (87% of theory).

Amino acid analysis of the purified N$^{60}$-Biotin-Pro-Gln-Gly-Ile-Ala-Gly-D-Arg-Lys-OH gave the following ratios: Gln 1:0; Pro 1.0; Gly 2.0; Ala 1.0; Ile 1.0; Lys 1.0: Arg 1.0; in agreement with theory.

Fast-atom bombardment mass spectrometry (FAB MS) gave a molecular ion mass peak of 1051, in agreement with theory.

The purified peptide was labeled as follows with a fluorescent marker at the C-terminal end of use in the assay method.

The purified peptide (1.27 g, 1.21 mmole) was dissolved in 100 ml of 0.1M sodium borate, pH 9.5, with stirring. Next, a solution of 3 g of fluorescein isothiocyanate (7.7 mmole) in 15 ml of DMSO was added to the peptide solution in ten equal portions over the course of two hours. After addition was complete, the reaction mixture was stirred for one hour and the pH of the mixture was adjusted to 7.5 with 5N HCl. The precipitate which formed was separated from the reaction mixture by centrifugation.

The volume of the peptide solution remaining after separation of the precipitate was adjusted to 200 ml with 0.1M ammonium acetate, pH 7.5. The solution was filtered through a 0.22 micron filter and loaded onto a 2.2×25 cm column of Vydac C-18 which had been equilibrated with 0.1M ammonium acetate, pH 7.5:acetonitrile, 95:5 v/v. The peptide was eluted from the column with a 855 minute linear gradient of 5% to 25% acetonitrile at a rate of 2 ml/min with collection of fractions. Analytical HPLC was used to identify fractions with the desired product. Fractions containing the peptide were pooled, frozen and lyophilized to yield 594.7 mg (34% of theoretical yield) of the title fluoresceinylated peptide.

Amino acid analysis of the purified peptide gave the following; Gln 1.0; Pro 1.0; Gly 2.0; Ala 1.0; Ile 1.0; Lys Lys 1.0; Arg 1.0; in agreement with theory. Fast-atom bombardment mass spectrometry gave a molecular ion mass peak of 1443, in agreement with theory.

Preparation 2

N$\alpha$-Biotin-Gly-Ser-Gln-Asn-Tyr-Pro-Ile-Val-Gly-Lys(N$\epsilon$-FITC)-OH (Seq. I.D. No. 4)

Substrate for HIV Protease

The protected peptide-resin N$\alpha$-Boc-Gly-Ser-Gln-Asn-Tyr(BrZ)-Pro-Ile-Val-Gly-Lys(2-CIZ)-CH$_2$-PAM-(Seq. I.D. No. 4) resin was synthesized on an Advanced Chemtech Model 200 peptide synthesized at 1.5 millimole scale using the standard double-couple protocol. The amino terminal Boc group was removed with 50% CF$_3$COOH/CH$_2$Cl$_2$ and the resulting resin neutralized with 5% diisopropylethylamine (DIEA) in CH$_2$Cl$_2$. Then 1.1 grams of biotin (4.5 mmoles) was dissolved in 20 mL of dimethyl sulfoxide and the solution added to the peptide resin. Then, 4.5 mmoles of DCC in 9 mL of CH$_2$Cl$_2$ was added to the resin and the reaction mixture brought to 40 mL total volume with 11 mL CH$_2$Cl$_2$. The coupling reaction was allowed to run for a total of 5 hours. The reaction solution was removed, the resin washed with DMSO, DMF and CH$_2$Cl$_2$, the resin neutralized with 5% DIEA in CH$_2$Cl$_2$, and the reaction repeated twice more with the reaction time being extended to 12 hours per reaction. Ninhydrin analysis of the resin indicated complete reaction of the biotin with the glycine amine group. The final peptide resin was washed extensively with DMF and CH$_2$Cl$_2$ and dried. Final yield=4.3 g (98% of theoretical).

The peptide was deprotected and cleaved from the resin using 50 ml of HF/m-cresol (9:1), 0° C., 1 hour. After removal of the HF by vacuum distillation, the m-cresol was extracted from the reaction mixture with 100 mL diethyl ether. The peptide was solubilized in 50% aqueous acetic acid, frozen and lyophilized. Final yield =2.4 g.

The crude N$\alpha$Biotin-Gly-Ser-Gln-Asn-Tyr-Pro-Ile-Val-Gly-Lys-OH (Seq. I.D. No. 4) was dissolved in 200 mL of 0.1% CF$_3$COOH in 95:5 H$_2$O:CH$_3$CN, filtered through a 0.22 micron filter and applied to a 2.2×25 cm. reverse-phase column of octadecyl-silica (Vydac C-18) which had been equilibrated with the same buffer. The peptide was eluted with a 855 minute linear gradient of 7.5 to 25% CH$_3$CN at 2 mL/minute with collection of fractions. Analytical high-performance liquid chromatography was performed on a 4.6×250 mm Vydac C-18 column using similar buffer conditions to analyze the column fractions. Column fractions containing the desired material were pooled, frozen and lyophilized. Final yield=1.206 g (62% of theory).

Amino acid analysis of the isolated N$^\alpha$Biotin-Gly-Ser-Gln-Asn-Tyr-Pro-Ile-Val-Gly-Lys-OH (Seq. I.D. No. 4 gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

The purified peptide was labeled as follows with a fluorescent marker at the C-terminal end for use in the assay. N$^\alpha$Biotin-Gly-Ser-Gln-Asn-Tyr-Pro-Ile-Val-Gly-Lys-OH (Seq. I.D. No. 4) (1.206 g, 0.936 mmoles) was dissolved in 100 mL of 0.1M sodium borate, pH 9.5 with stirring. Then, 3 g of fluorescein isothiocyanate (7.7 mmoles) was dissolved in 15 mL dimethyl sulfoxide and the solution added to the reaction in 10 equal portions over the course of a two hour period. The reaction was allowed to proceed for a further one hour after the final addition had been made. The pH of the solution was adjusted to 3 with 5N HCl. A precipitate which formed was removed from the reaction by centrifugation.

The pH of the remaining peptide solution was raised to 7.8 with 5N NaOH and the volume adjusted to 200 mL with 0.1M ammonium acetate, pH 7.5. The peptide solution was filtered through a 0.22 micron filter and loaded onto a 2.2×25 cm column of Vydac C-18 which had been equilibrated with 95:5 0.1M ammonium acetate, pH 7.5:CH$_3$CN. The peptide was eluted from the column with a 855 minute linear gradient of 5 to 25% CH$_3$CN, 2 mL/minute with collection of fractions. Analytical HPLC was used to identify fractions with the desired material which were then pooled, frozen and lyophilized. Final yield=190.2 mg (12% of theoretical).

Amino acid analysis of the purified peptide gave the following: Asn 1.1; Ser 1.0; Gln 1.1; Pro 1.1; Gly 2.1; Val 0.8; Ile 0.8; Tyr 1.1; Lys 1.0; in agreement with theory. Fast-atom bombardment mass spectrometry gave a molecular ion mass peak of 1678, in agreement with theory.

Preparation 3

N$^\alpha$Biotin-Arg-Arg-Arg-Pro-Gln-Gln-Phe-Phe-Gly-Leu-Met-Gly-Lys-(N$^\epsilon$-FITC)-OH (Seq. I.D. No. 5)

Substrate for Vertebrate Stromelysin Assay

The protected peptide-resin, Boc-Arg(Tos)-Arg(Tos)-Arg(Tos)-Pro-Gln-Gln-Phe-Phe-Gly-Leu-Met(O)-Gly-Lys(2-ClZ)-OCH$_2$-PAM-resin (Seq. I.D. No. 5), was synthesized on an Advanced Ghemtech Model 200 peptide synthesizer at 1.5 millimole scale using the standard double-couple protocol. The amino terminal Boc group was removed with 50% trifluoroacetic acid in methylene chloride and the resulting resin was neutralized with 5% DIEA in methylene chloride. A solution of 1.1 g of biotin (4.5 mmole) in 20 ml of DMSO was added to the peptide resin. Next, a solution of 4.5 mmole of DCC in 9 ml of methylene chloride was added to resin solution containing the biotin and the reaction mixture was diluted to a total volume of 40 ml with 11 ml of methylene chloride. The biotin-peptide-resin coupling reaction was allowed to run for 5 h. The reaction solution was separated from the resin, the resin washed with DMSO, DMF and methylene chloride, and the resin neutralized with 5% DIEA in methylene chloride. The coupling reaction was repeated twice at an extended time of 12 hours per reaction. The sulfoxide of methionine was reduced directly on the resin with trifluoroacetic acid:dimethyl sulfide:HCl (9:1:1, v/v) according to the procedure of Heath et al. (1986) Int. J. Peptide Protein Res. 28 498–507. The peptide-resin was washed extensively with DMF and methylene chloride and was dried. The yield of N$^\alpha$Biotin-Arg(Tos)-Arg(Tos)-Arg(Tos)-Pro-Gln-Gln-Phe-Phe-Gly-Leu-Met-Gly-Lys(2-ClZ)-O-CH$_2$-PAM-resin (Seq. I.D. No. 5) obtained was 4.62 g (77% of theoretical).

The peptide was deprotected and removed from the resin with 66 ml of HF/m-cresol (9:1) at 0° C. for one hour. The hydrogen fluoride was removed from the reaction mixture by vacuum distillation and the m-cresol was extracted from the reaction mixture with 100 ml of diethyl ether. The peptide was solubilized in 50% aqueous acetic acid and the solution frozen lyophilized to yield 2.24 g of the deprotected biotinylated peptide in crude form.

The crude peptide, N$^\alpha$Biotin-Arg-Arg-Arg-Pro-Gln-Gln-Phe-Phe-Gly-Leu-Met-Gly-Lys-OH (Seq. I.D. No. 5), was purified as follows. The crude peptide was dissolved in 200 ml of 0.1% trifluoroacetic acid in 90:10, water:acetonitrile and the solution filtered through a 0.22 micron filter. The filtrate was supplied to a 2.2×25 cm reverse-phase column of octaclecylsilica (Vydac C-18) previously equilibrated with the same buffer. The peptide was eluted with a 740 min linear gradient of 10 to 22.5% acetonitrile in water at a rate of 2 ml/min. Multiple fractions were collected and assayed for peptide via analytical HPLC on a 4.6×250 mm Vydac C-18 column using similar buffer conditions. Fractions containing the desired peptide were pooled, frozen and lyophilized yielding 669 mg (29% of theory).

Amino acid analysis of the purified peptide gave the following ratios: Gln 2.0; Pro 1.0; Gly 2.0; Met 0.9; Leu 1.0; Phe 2.0; Lys 1.0; and Arg 3.0; in agreement with theory. Fast-atom bombardment mass spectrometry (FAB) gave a molecular ion mass peak of 1847, in agreement with theory.

The purified peptide was labeled with a fluorescent marker as follows. To a solution of 669 mg (0.35 mmole) peptide in 100 ml of 0.1M sodium borate, pH 9.5, was added in 10 equal portions over a two hour period a solution of 1 g (2.3 mmole) of fluorescein isothiocyanate in 15 ml of DMSO. After the final addition was completed the reaction was allowed to proceed for one hour. The pH of the reaction solution was lowered to 7.5 with 5N HCl and the precipitate which had formed was removed by centrifugation. The volume of the fluoresceinylated peptide was adjusted to 200 ml with 0.1M ammonium acetate, pH 7.5. The diluted solution was filtered through a 0.22 micron filter and loaded onto a 2.2×25 column of Vydac C-18 which had been equilibrated with 95:5 0.1M ammonium acetate, pH 7.5:acetonitrile, v:v. The peptide was eluted from the column with an 855 minute gradient of 50% to 25% acetonitrile at a rate of 2 ml per minute with collection of fractions. Analytical HPLC was used to identify the fractions containing the desired product. These fractions were pooled, frozen and lyophilized. Final yield=406 mg (52% of theoretical) of N$^{60}$-Biotin-Arg-Arg-Arg-Pro-Gln-Gln-Phe-Phe-Gly-Leu-Met-Gly-Lys(N$^\epsilon$-FITC)-OH. (Seq. I.D. NO. 5)

Amino acid analysis of the purified peptide gave the following ratios: Gln 2.0; Pro 1.0; Gly 2.0; Met 1.0; Leu 1.0; Phe 2.0; Lys 1.0; Arg 3.0; in agreement with theory. Fast atom bombardment mass spectrometry gave a molecular iron mass peak of 2239 in agreement with theory.

The following describes the compositions of the reagents (buffers and solutions) used and referred to in the following Examples.

| | |
|---|---|
| MES-ALB Buffer | 0.05 M 4-morpholinesulfonic acid, pH 5.5 |
| | 0.02 M NaCl |
| | 0.002 M EDTA |
| | 0.001 M DTT |
| | 1.0 mg/ml BSA |
| TBSA Buffer | 0.02 M Tris |
| | 0.15 M NaCl |
| | 1.0 mg/ml BSA |
| Buffer A | 100 mM HEPES, pH 7.5 |
| | 100 mM TAPS, pH 7.5 |
| | 10 mM Calcium acetate |
| | 1.0 mg/ml BSA |
| Buffer B: | 100 mM Tris-HCl |
| | 100 mM EDTA |
| | 1 mg/ml BSA |
| | pH 7.5 |
| Avidin Coated Beads Solution | 0.1% solution Fluoricon Avidin Assay Particles (Avidin conjugated to solid polystyrene beads, 0.6–0.8 microns in diameter in TBSA Buffer |
| Enzyme Solution | 27 IU/ml of HIV-1 protease in MES-ALB buffer (1 IU equals the amount of enzyme required to hydrolyze 1 μmole of substrate per minute at 37° C.) |

EXAMPLE 1

HIV-1 Protease Inhibitor Assay Procedure

To each well of a round bottom, 96-well plate is added 20 μl of the HIV-1 protease Enzyme Solution followed by 10 μl of the inhibitor compound in 20% aqueous DMSO. The solution is incubated for one hour at room temperature before 20 μl of a solution of the substrate $N^\alpha$-Biotin-Gly-Ser-Gln-Asn-Tyr-Pro-Ile-Val-Gly-Lys($N^\epsilon$-FITC)-OH, (Seq. I.D. No. 4) in MES-ALB buffer (1.5 μl/ml) is added to each well. The solutions are incubated for 16 hours at room temperature and thereafter to each well is added 150 μl of MES-ALB buffer.

To each well of 96-well Pandex plate is added 25 μl of the Avidin coated beads solution. Next, 25 μl of the diluted incubation solutions are added to each well of the Pandex plate, the solutions are mixed well and the plates are loaded into the Pandex machine, washed, evacuated and read. EXAMPLE 2

Collagenase Assay Procedure

To each well of a 96-well plate is added 50 μl of a solution of the substrate, $N^\alpha$-Biotin-Pro-Gln-Gly-Ile-Ala-Gly-D-Arg-Lys($N^\epsilon$-FITC)-OH, at 15 μg/ml in Buffer A, 50 μl of cell conditioned medium, and 50 μl of a 1.5 mM solution of 4-aminophenylmercuric acetate in Buffer A. The mixed solutions are incubated at 37° C. for 16 hours in a humidified incubator and then, 20 μl of the solution in each of the 96 wells is transferred to a fresh 96-well plate. The solutions are diluted with 180 μl of Buffer B and are then incubated at room temperature for 30 minutes.

To each well of a 96-well Pandex plate is added 25 μl of Avidin coated beads solution and 25 μl of the diluted reaction solutions is added to each well of the Pandex plate and the solutions mixed well with the Pandex plate and the solutions mixed with the Avidin coated beads solution. The plates are loaded into the Pandex machine and the plates are washed with TBSA Buffer and then are read.

EXAMPLE 3

Stromelysin Assay Procedure

The assay procedure of collagenase described by Example 2 is used in assaying for stromelysin by substituting prostromelysin for procollagenase and the stromelysin substrate, $N^\alpha$-Biotin-Arg-Arg-Arg-Pro-Gln-Gln-Phe-Phe-Gly-Leu-Met-Gly-Lys($N^\epsilon$-FITC)-OH (Seq. I.D. NO. 5) for the collagenase substrate.

We claim:

1. A polypeptide selected from the group consisting of R-Gly-Ser-Gln-Asn-Tyr-Pro-Ile-Val-Gly-Lys-(R')-OH (SEQ ID NO: 4), R-Pro-Gln-Gly-Ile-Ala-Gly-D-Arg-Lys-(R')-OH, and R-Arg-Arg-Arg-Pro-Gln-Gln-Phe-Phe-Gly-Leu-Met-Gly-Lys-(R')-OH (SEQ ID NO: 5), wherein R is biotinoyl or FITC and R' is biotinoyl or FITC, provided that when R is biotinoyl, R' is FITC, and when R is FITC, R' is biotinoyl.

2. A polypeptide of claim 1 wherein R is biotinoyl and R' is FITC.

* * * * *